(12) United States Patent
Maddess et al.

(10) Patent No.: US 6,315,414 B1
(45) Date of Patent: Nov. 13, 2001

(54) SIMULTANEOUS BINOCULAR ASSESSMENT OF MULTIPLE OPTIC NERVE AND CORTICAL REGIONS IN DISEASES AFFECTING NERVE CONDITION

(75) Inventors: Teddy Lee Maddess, Kaleen; Andrew Charles James, Braddon, both of (AU)

(73) Assignee: Australian National University, Canberra (AU)

( * ) Notice: Subject to any disclaimer, the term of this patent is extended or adjusted under 35 U.S.C. 154(b) by 0 days.

(21) Appl. No.: 09/647,357
(22) PCT Filed: Mar. 30, 1999
(86) PCT No.: PCT/AU99/00230
  § 371 Date: Dec. 21, 2000
  § 102(e) Date: Dec. 21, 2000
(87) PCT Pub. No.: WO99/49776
  PCT Pub. Date: Oct. 7, 1999

(30) Foreign Application Priority Data

Mar. 30, 1998 (AU) .............................................. PP2661/98

(51) Int. Cl.[7] ...................................................... A61B 3/00
(52) U.S. Cl. ........................................... 351/246; 600/558
(58) Field of Search ..................................... 351/209, 210, 351/211, 222, 246; 600/544, 27, 558

(56) References Cited

U.S. PATENT DOCUMENTS

| | | |
|---|---|---|
| 4,832,280 | 5/1989 | Kornacker . |
| 5,474,081 | 12/1995 | Livingstone et al. . |
| 6,086,206 * | 7/2000 | Sutter .................................. 351/224 |

* cited by examiner

Primary Examiner—George Manuel
(74) Attorney, Agent, or Firm—Nixon Peabody LLP; Donald R. Studebaker

(57) ABSTRACT

This invention concerns the detection of neural damage to the optic nerve, optic radiations and white matter of the visual brain indicative of various neurological disorders but with particular application to multiple sclerosis. The method involves simultaneous measurement of the shape and latency of responses to visual stimuli presented simultaneously in different parts of the visual field of the two eyes, separating out linear and nonlinear response components, and most particularly separating out binocular interaction responses to assess neural function within each half of the visual cortex. Because rough retino-topicity is maintained in the optic nerve, through the optic radiations and the visual cerebral cortex, stimulation of the separate parts of the visual field permits isolation of responses from different component parts of these neural elements and therefore from the results obtained an objective assessment of damage to these separate neural components can be made simultaneously.

15 Claims, 6 Drawing Sheets

SIMULTANEOUS BINOCULAR ASSESSMENT OF MULTIPLE OPTIC NERVE AND CORTICAL REGIONS IN DISEASES AFFECTING NERVE CONDITION

TECHNICAL FIELD

This invention concerns the detection of neural damage to the optic nerve, optic radiations and white matter of the visual brain indicative of various neurological disorders but with particular application to multiple sclerosis.

BACKGROUND ART

Diseases such as multiple sclerosis reduce the effectiveness of neural transmission. A common diagnostic technique in these diseases is to measure electrical potentials evoked in response to various forms of stimulation of peripheral sensory nerves: abnormally long neural conduction times being equated with neural disease. Neurones concerned with conducting neural signals over longer distances are typically assisted in their conduction by a sheath of insulative material known as myelin. Diseases such as multiple sclerosis disrupt the myelin sheath and thereby impair the speed of neural conduction. Such changes in nerve conduction latency and other changes in the time-course of the evoked potential can be observed in a variety of other disorders such as optic neuritis, various optic atrophies, toxic amblyopia, papilledema, Parkinson's, tumours, migraine, various ataxias, compression of the visual nerves, spinocerebellar degenerations and Vitamin $B_{12}$ deficiency as described in the paper by S. Sokol, entitled "The visually evoked cortical potential in the optic nerve and visual pathway disorders", which was published in *Electrophysiological testing in diseases of the retina, ootic nerve, and visual pathway*, edited by G. A. Fishman, published by the American Academy of Ophthalmology, of San Francisco, in 1990, Volume 2, Pages 105–141.

The evoked potentials (EPs) conventionally measured reflect the activity of large bundles of neurones contained within a nerve. Thus the EP represents a gross sum of many cells' activity. Such a gross sum would tend to mask the effects of small focal lesions to smaller subsets of neurones within the nerve, such as those found in multiple sclerosis, since responses from neurones with damaged and intact myelin are summed together. Therefore it would be desirable to obtain different EP responses produced by different component parts of a nerve in order to highlight focal neural damage.

In more recent times Magnetic Resonance Imaging has provided a method to obtain images at least of the larger focal lesions found in multiple sclerosis. Studies comparing the relative sensitivities and specificities of MRI with a variety of Evoked Potential (EP) methods, including Visual (VEP), Auditory (AEP) and Somatosensory (SEP) methods, reveal that MRI is superior to the EP methods in diagnosing MS as described in the paper by T. Sand and I.A. Sulg, entitled "Evoked potentials and CSF-immunoglobulins in MS: relationship to disease duration, disability, and functional status", which was published in *Acta Neural Scand*, Volume 82, Pages 217–21, and the paper by HI.A van Diemen, P. Lanting, J.C. Koetsier, R.L. Strijers, H.K van Walbeek and C.H. Pornan, entitled "Evaluation of the visual system in multiple sclerosis, a comparative study of diagnostic tests", which was published in *Clin Neurol Neurosurge*, Volume 94, Pages 191–5. Of these various EP methods the VEP comes closest to matching the performance of $MRI_1$, VEP sensitivity rarely lagging MRI by more than 10% as described in the paper by M. Ravnborg, R. Liguori, P. Christiansen, H. Larsson and P.S. Sorensen, entitled "The diagnostic reliability of magnetically evoked motor potentials in multiple sclerosis", which was published in *Neurology*. Volume 42, Pages 1296–301. As pointed out above part of the failing of the EP methods is undoubtedly that the measured potentials commonly represent a sum over the whole of whichever particular sensory pathway is stimulated. In the case of the VEP some differential measurement is often attempted by using stimuli consisting of checkerboard patterns of different scales, the idea being that finer patterns bias the VEP somewhat towards measurements from the central retina and visual field as described in the paper by M.R. Harter, entitled "Evoked cortical responses to checkerboard patterns; effect of check-size as a function of retinal eccentricity", which was published in *Vision Res*, Volume 10, Pages 1365–76. Attempts have been made to characterise responses from each hemifield separately and to try to achieve some separation of hemispheric responses by use of widely displaced pairs of electrodes as reported in the paper by L.D. Blumhardt, G. Barrett, A.M. Halliday and A. Kriss, entitled "The effect of experimental 'scotomata'on the ipsilateral and contralateral responses to pattern-reversal in one half-field", which was published in *Clin. Neurophvsiol.*, Volume 45, Pages 376–392. Inadequate isolation of these responses, in conjunction with different recording electronics and different recording times for the compared responses contribute to less than satisfactory results. Nevertheless, given the close concordance between VEP and $MRI_1$, an improved VEP, provides the best promise of performance comparable to MRI that could be done in the average neurologist's surgery as often as desired and at lower cost.

DISCLOSURE OF THE INVENTION

The prime objective of the present invention is the provision of a simultaneous, rapid, reliable test for damage to nerve conduction in component parts of the optic nerve, optic radiations and visual cortex. This objective is achieved by presenting visual stimuli, to parts of the visual field such that component parts of the optic nerve, optic radiations and visual cortex are roughly separately stimulated and with the temporal structure of the stimuli applied to each visual field region being sufficiently complex in their temporal characteristics to permit estimation of linear and nonlinear weighting functions such as Wiener or Volterra kernels to characterise the linear (first order) and nonlinear (second order) responses of each component part of the optic nerve, optic radiations and visual cortex.

In broad form the present invention provides a method of simultaneously assessing the presence of damage to component parts of the optic nerve, optic radiations and visual cortex, the method including the steps of.

(a) dividing the visual field of view of each eye into a plurality of zones so as to roughly isolate confluent streams within the optic nerve, optic radiations and visual cortex due to their retinotopic arrangement;

(b) presenting to the two eyes stimuli having different temporal modulation of the appearance of each of the zones of the visual field of each eye, the stimuli being different for each of the corresponding zones within the visual field of view of each eye, (c) making the temporal content of the variations of the appearance of the time varying stimuli sufficiently complex as to permit estimation of linear and nonlinear weighting functions characterising measured responses to each stimulus region and for each eye;

(d) estimating some or all of the coefficients of the linear and nonlinear functions, for each stimulus zone, and binocular interaction, from the measured responses to said stimuli, to isolate separate contributions from component parts of the optic nerve, optic radiations and the left and right halves of the visual brain simultaneously.

Preferably, the linear and nonlinear weighting functions are Weiner or Volterra kernels.

As will be apparent the test involves measuring kernels which characterise the linear and nonlinear responses of component parts of the optic nerve, optic radiations and visual cortex in response to simultaneous stimulation of different parts of the visual field. The invention provides for the measurement of nerve conduction information, such as the conduction delay to the peak measured kernel response, for both first and second order responding nerve components and computation of binocular interaction kernels to isolate simultaneously generated kernel responses to dichoptic stimulation of the two eyes with different temporal sequences of light flashes whose temporal structure is sufficiently complex to permit calculation of the requisite kernels. Other aspects of the time-course of the kernels obtained for each part of the optic nerve, optic radiations and visual cortex or comparisons between the responses obtained between component responses can also be utilised. It is important to note that the present invention allows separate assessment of visual cortical responses and those from the optic nerve and optic radiations.

The method can be further extended by simultaneous presentation of stimuli through other sensory modalities such as tactile or auditory stimuli, having similar temporal characteristics, and computing interaction kernels between the modalities to isolate responses from brain regions where these sensory modalities interact, Visual stimulation is of primary interest because of the large number of neurones in the visual pathway and the close concordance between VEP and MRI as compared to EPs from other sensory modalities.

In a preferred method the visual field is divided into a zone centred on the central 6 to 12 degrees of the central visual field of view, and at least 4 surrounding zones splitting the more peripheral visual field into quadrants defining the superior-nasal, superior-temporal, inferior-temporal and inferior nasal peripheral visual field.

Preferably, the latency to selected peaks within time course of the linear kernels is used as a measure of nerve conduction time with the component part of the optic nerve and optic radiations. Other measures of the structure or shape of the kernel can also be used.

In a further preferred form, the latency to some or all of the peaks along the diagonals of the second order self quadratic kernels, and or selected portions of higher order kernels can be used to characterise different nonlinear responses such as ON-OFF responses characteristic of sub-populations of neurones within the optic nerve. This is possible because each diagonal characterises interactions between pairs of stimuli presented at different mutual delays.

Preferably, estimated binocular interaction kernels are compared with those obtained from normal subjects to identify nerve conduction defects which would be characteristic of damage within each hemicortex.

In a preferred method, the computation of hemicortical delays is repeated separately for the separate zones, more preferably the inferior and superior zone of each half of the visual field.

The estimates of the kernel coefficients are preferably obtained by means of logistic or linear regression and or iterative methods permitting estimates of the errors in the coefficients to be made. Preferably, the coefficients are expressed as measures such as t-statistics rather than physical measures with units such as volts.

In a preferred method, the temporal stimulus sequences will modulate the brightness of elements within each of the stimulus zones between two or three brightness levels where the function governing the alternation between the levels is approximately uniformly distributed noise.

In accordance with a further preference the stimuli can be extended to other sensory modalities presented simultaneously, where the temporal characteristics of these other stimuli are like those of each of the visual stimuli and interaction kernels between each of the visual field zone stimuli and the other sensory modalities, and each of the other modalities, are also computed to isolate brain responses from brain regions where those sensory modalities interact.

Also, persons skilled in the art will recognise that evoked neuronal responses may be recorded by means other than by measuring electrical potentials such as by recording changes in magnetic, or electromagnetic radiation, or acoustic signals.

The invention will be further described, by way of example only, with reference to the accompanying drawings.

BRIEF DESCRIPTION OF THE DRAWINGS

FIG. 4(c) corresponds to the right eye. FIG. 4(b) shows the binocular interaction kernels (solid lines).

BEST MODES FOR CARRYING OUT THE INVENTION

Figure 1:
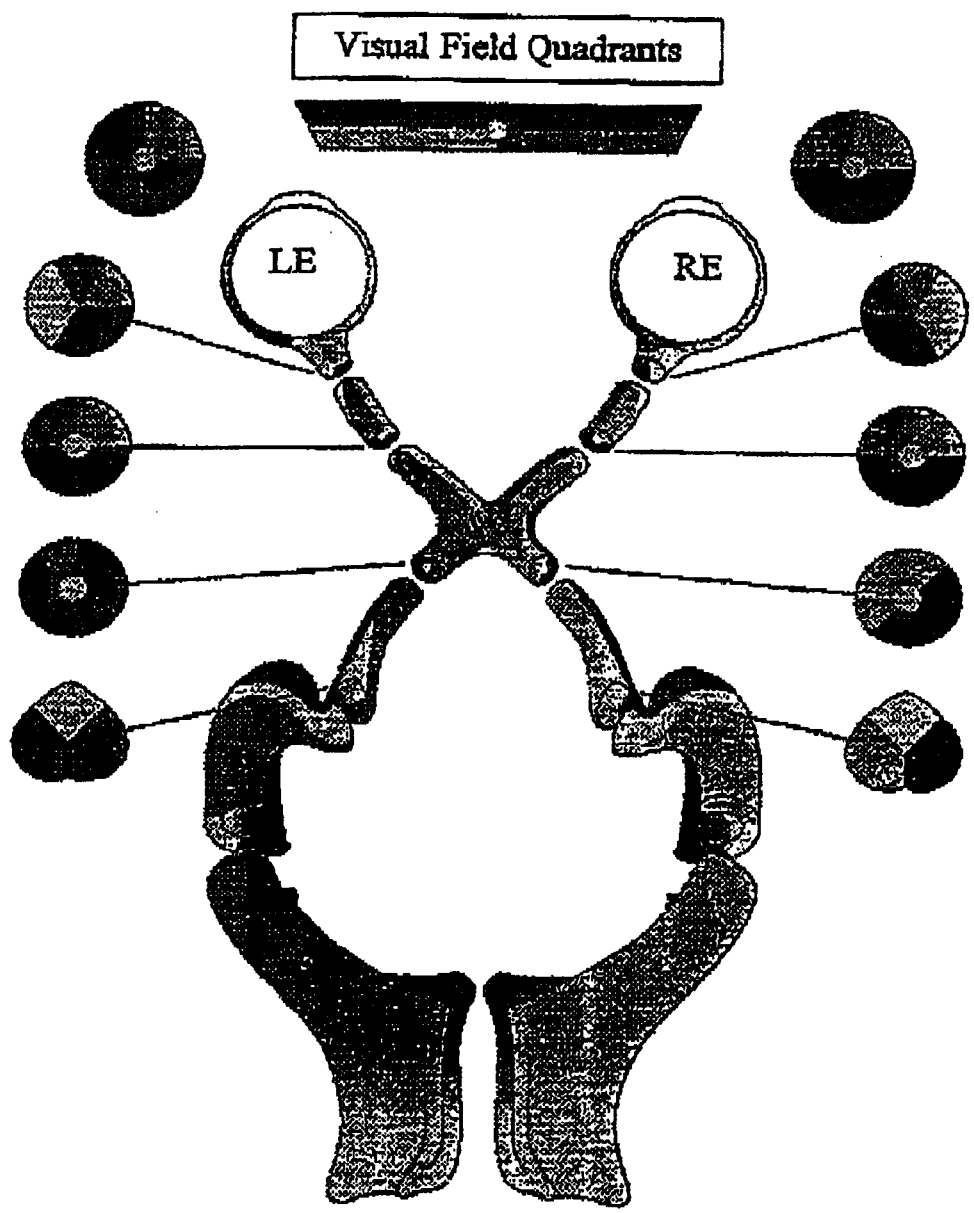
FIG. 1 schematically shows how the visual field maps onto the retina.

As noted above VEPs would likely be enhanced if separate measures could be obtained from different component parts of the optic nerve. Fortunately when the nerves of the retina exit the eye they maintain much of their relative positions within the nerve. Thus a transection of the nerve would show that the nerves within a given quadrant of the circular cross section would come from the same quadrant of the eye as indicated in FIG. 1. Therefore stimulating a given part of the visual field stimulates a given part of the retina and so in turn a subsection of the optic nerve. This maintenance of retinal positional order of the component neurones is known as retinotopicity.

The nerves making up the optic nerve are also not all of the same type but come in several classes. A major differentiating feature of some of these classes is the relative linearity or nonlinearity of their responses to light and also their neural conduction speed as described in the paper by E. Kaplan and R. M. Shapley, entitled "The primate retina contains two types of ganglion cells, with high and low contrast sensitivity", which was published in *Proc. Nati. Acad. Sci. USA*, Volume 83, Pages 2755–2557, and the paper by R. T. Marrocco, J. W. McClurkin and R. A. Young, entitled "Spatial summation and conduction latency classification of cells of the lateral genicufate nucleus of macaques", which was published in *J. Neuroscience*, Volume 2, Pages 1275–1291. Thus, the gross EP potential is the sum of component potentials from neurones having different conduction delays. Separation of linearly and nonlinearly responding neurones would thus further disentangle the signals summed in the gross VEP.

Another consideration is that the neurones from optic nerves of the two eyes can have different destinations in the brain. In particular the optic nerves meet at the chiasm and then reassemble into the optic radiations before reaching the cerebral cortex. Some neurones cross to enter the cerebral cortex on the opposite side of the head while others continue straight to the cerebral cortex of the same side of the head. FIG. 1 schematically shows how the visual field, see rectangle at top of figure labelled visual field, when divided into the central visual field and the four surrounding quadrants superior nasal, superior temporal, inferior temporal and inferior nasal, maps onto the retina. The confluence of optic nerve fibres then maintain a rough retinotopic map as they travel into the optic nerve and then, following the chiasm, the optic radiations and the two visual hemi-cortices. The effect of this decussation is that neurones receiving visual stimulation from the left visual field of both eyes travel to the right visual cortex, while neurones receiving visual stimulation from the right visual field of both eyes travel to the left visual cortex. The decussation of the optic nerves permits the binocular interactions required for the perception of depth through stereoscopic vision. The binocular interactions in the cortex pose problems for persons measuring VEPs given that typically only one electrode set is used and isolation of responses on the two sides of the brain is little improved by the use of further electrodes placed at different locations on the scalp. It would therefore be highly desirable to separate out binocular neural response associated with binocular function within each of the two sides of the cortex and assess those responses for conduction delays and other defects produced by impaired neural transmission brought about by diseases such as multiple sclerosis.

Linear systems can be fully characterised by the response of the system to a brief impulsive stimulus. The resulting impulse response or kernel can then be used to accurately predict the response of the system to any arbitrary stimulus by simply convolving the stimulus sequence with the kernel. The kernel thus embodies a complete description of the system. Nonlinear systems cannot be characterised in this way because the nonlinearities will lead to interactions between stimulus components that cannot be characterised by the response of the system to a single event. All pairwise interactions could be characterised by testing with every possible pair of stimuli. In the case of a flashing light stimulus in a visual system this would correspond to testing every possible set of latencies between two flashes to look for facilitation and ON-OFF responses. Responses are said to be ON-OFF if equal responses are obtained to the onset and offset of a flash, as would be generated by a quadratic response nonlinearity. Obviously such an exhaustive search would be very time consuming and would leave the difficulty of how to piece all that information together to predict the response of the nonlinear system to an arbitrary stimulus to demonstrate that the nonlinear system had been adequately characterised.

A far better situation-would be if quite arbitrary stimulus sequences could be presented which would permit information about the response of the nonlinear system to be encapsulated in something like the kernel of a linear system. Ideally, any linear and nonlinear response components also should be separately characterisable. Nonlinear Systems Identification (NSI) provides exactly that. In particular, methods which permit the estimation of Wiener Kernels provide a so called orthogonal decomposition where there is no correlation between the kernels characterising linear, quadratic, cubic etc. interactions of the system under study. The method also permits multiple stimuli to be presented, and separate kernels describing the linear and nonlinear responses to each stimulus, and further kernels describing any interactions between the stimuli, to be obtained. These kernels are explained more formally below.

The following equation defines the model response of a linear system receiving a single input stimulus:

$$r(t) = \int_0^M k(t_1) s(t - t_1) dt_1 \quad (1)$$

where $r(t)$ is the response at time $t$, $s(t-t_1)$ is the stimulus at preceding time $t-t_1$, $k(t_1)$ is the kernel value, giving the weight for the lag $t_1$, and weighted stimulus values are integrated from lag zero up to the effective memory length of the system, M.

This archetypical system model is elaborated in the following ways. First, a number of input stimulus signals are considered, corresponding to the different zones of visual stimulation, and to stimulation via the left and right eyes, presented by the dichoptic method. If the stimulus channels are indexed as $s_1, s_2, \ldots, s_n$, the first-order response component is now:

$$r_1(t) = \sum_{i=1}^n \int_0^M k_i(t_1) s_i(t - t_1) dt_1 \quad (2)$$

Secondly, response components are added which are second-order, or bilinear, in each of the stimulus signals:

$$r_1(t) = \sum_{i=1}^n \int_0^M \int_0^M k_{ii}(t_1, t_2) s_i(t - t_1) s_i(t - t_2) dt_1 dt_2 \quad (3)$$

where $k_{ii}(t_1,t_2)$ is the second-order kernel, weighting the stimulus product $s(t-t_1) s(t-t_2)$, for the pair of lag values $t_1,t_2$, and the weighted stimulus values are integrated over all pairs of lags, $t_1,t_2$ from zero up to the effective memory-length, M.

Thirdly, interaction terms are added modelling second-order interaction between certain of the stimulus channels, in particular between the corresponding regions of visual field presented via left and right eye. For channels $s_i$, and $s_j$, the interaction term is:

$$r_{ij}(t) = \int_0^M \int_0^M k_{ij}(t_1, t_2) s_i(t - t_1) s_j(t - t_2) dt_1 dt_2 \quad (4)$$

These kernels, $k_{ij}$ are called the Binocular Interaction Kernels, or BIKs. As the signals from each eye first come together in the visual cortex, the BIKs reflect signal transformation that can be inferred to be at the cortical level, and not earlier in the optic, nerve or optic radiations.

The resulting model, formed by summing all these terms, relates the applied stimulus signals, with the recorded response, r(t), by means of unknown weighting functions, or kernels, $k_i$, $k_{ii}$, and $k_{ij}$. The resulting model, whilst nonlinear in the stimulus signals due to the second order products, is still linear in all kernel values. Linear regression techniques are used to form the least-squares estimates of these kernels, at the sampling interval used in recording, thus characterising the relative latency and sensitivity of response to the stimulus fields of each eye, and also the second-order response to each region, and the interaction term between corresponding regions of each eye. By extension it can be seen that higher order kernels characterising higher order response nonlinearities may also be estimated.

Considering firstly stimuli presented over time the first order (linear) kernels $k_i$, are one dimensional functions, as can be seen from equation 2. In the case of flashes presented to the component parts of the visual field the kernels obtained are like the impulse responses of the visual system in the sense that convolution with an arbitrary stimulus yields a highly accurate prediction of the linear response of the system to the arbitrary stimulus sequence. The shape of the kernel provides information about the latency and gain of the linear response just as the response to a repeated train of short flashes would except that any nonlinear response that might confound interpretation has be removed.

The second order kernels ($k_{ii}$) are 2 dimensional, as can be seen from Equation 3: given that they are sets of numbers character within a set duration, that is the memory length (M) of the system, As such $k_{ii}$ would for example characterise ON-OFF responses. To obtain the full predicted response to an arbitrary stimulus these two traces, obtained by convolutions between that stimulus and $k_i$ and $k_{ii}$, are simply added.

It is apparent that even such a simple characterisation would be an improvement over a normal VEP in that separate latencies for largely linear and largely ON-OFF ganglion cells in the optic nerve could be obtained. One limitation is that the number of coefficients estimated in the various kernels should not exceed the number of stimulus events obtained in the recording process. Thus, it is best to keep the number of regions small. Methods such as linear regression or iterative methods can be used to estimate only a selected subset of the coefficients to keep their number small.

Such a stimulus system is in part the basis of the proposed method and device with the added innovative feature of exploiting the retinotopicity of the optic nerve and optic radiations to obtain separate kernels for each component part of the nerve and the further innovative feature of dichoptic presentation of different stimuli to each eye for the purpose of simultaneously obtaining kernels for each of the left and right halves of the cerebral cortex, that is for each hemicortex. To achieve these objectives the visual field is split into nasal and temporal stimulus subregions permitting the possibility of measuring separate signals for conduction within each hemicortex given that information from the left visual field of the two eyes is combined for the first time in the right hemicortex, as shown in FIG.1, and visa versa for the right visual field. To achieve this separate signals are simultaneously provided to the two eyes.

This can be achieved by use of a system such as a liquid crystal frame shutter. The shutter covers the whole of the visual display device and transmits left or right circularly polarised light for each alternate frame in the stimulus sequence. The subjects wear passive glasses containing a quarterwave plate and dichroic filters. This system permits separate video images to be sent to both eyes and the degree of isolation of the dichoptic stimuli is preserved even with head rotation. Thus on each alternate frame differing, temporally orthogonal signals will be sent to each eye for each region. With this stimulus system it is possible to calculate from the recorded evoked response, binocular interaction (BIK, pronounced bike) kernels $k_{ij}$ as described in equation 4, for each stimulus region. The retinotopicity of the optic nerve system can be further exploited by splitting the visual field into inferior and superior parts. A person skilled in the art will appreciate that different means of generating separate signals for the two eyes, whether these be optical means, employing separate stimulus display devices to the two eyes, or by holographic means, can also be used.

In the simplest case of stimuli presented to the left superior and inferior visual fields and the right inferior and superior visual fields notice that the BIK kernels for the two left visual fields characterise a (binocular) signal only found in the right hemicortex (and some parts of the thalamus). Similarly the 2 BIK kernels from the right hemifield characterise nerve conduction processes in the left hemicortex. Thus, a completely new type of information is provided by the invention. In practice one or more separate regions can occupy the central few degrees of the visual field.

In the examples below neural responses are characterised to the stimuli by measuring evoked electrical potentials. Persons skilled in the art will recognise that evoked neuronal responses may be recorded by means other than by measuring electrical potentials such as by recording changes in magnetic, or electromagnetic radiation, or acoustic signals.

In addition to the BIK data, and temporal interaction data, the method according to this invention permits the measurement of separate latency and amplitudes for linear and ON-OFF nerve components for several component parts of the optic nerve and radiations. Separation of these component signals provides improvement over the gross method of effectively averaging all these signal components as currently occurs with conventional VEPs. It is amazing that standard VEPs are nearly as effective as MRII the corollary of which is that the new method has the potential to be as good or better than MRI.

EXAMPLES

Figure 2:
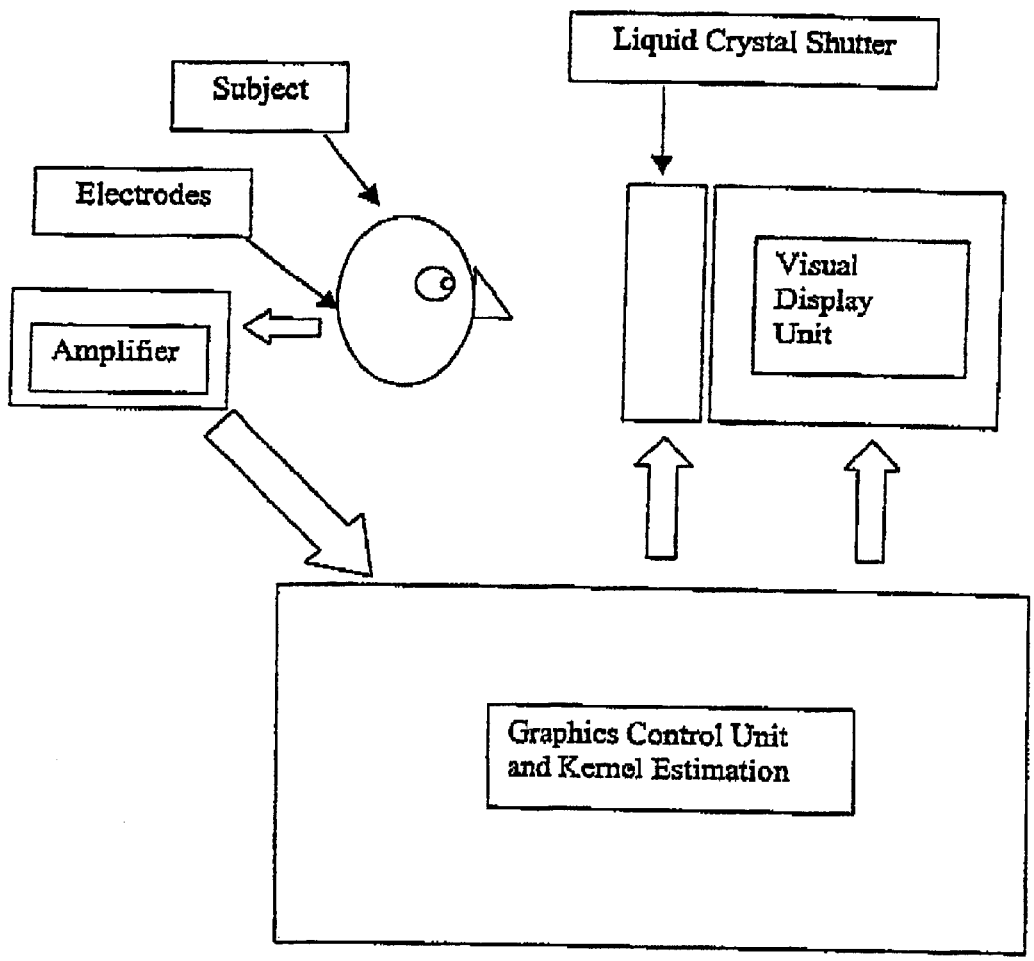
FIG. 2 shows a schematic outline of the basic system components forming an apparatus for simultaneously assessing the effectiveness of neural conduction within the various parts of the optic nerve, optic radiations and visual cortex according to this invention.

FIG. 2 shows a schematic scheme of the basic system components forming an apparatus for simultaneously assessing the effectiveness of neural conduction within the various parts of the optic nerve, optic radiations and visual cortex corresponding to different parts of the visual field. The major components are an apparatus for dichoptic stimulation of the two eyes, in the present non-limiting example by means of a liquid crystal shutter, a means for assessing cortical neural responses, in the present example electrodes and an amplifier for recording a visual evoked electrical potential, and a means for computing estimates of kernel coefficients. Thin arrows associate labels with objects while thick block arrows indicate the direction of information flow or control.

Normal subjects and subjects diagnosed with definite multiple sclerosis were compared. The test stimuli for each subject were presented on a video monitor at 101 pictures per second. Since the stimuli were presented on a video monitor it is common to refer to the sequence of pictures presented as a sequence of frames presented at a particular frame rate, in this case 101 frames per second. The stimulus sequence consisted of a stream of separate, but temporally interleaved, images presented alternately to each eye at 50.5 frames per second by use of a liquid crystal shutter. Presentation of separate images to the two eyes is referred to as dichoptic presentation. To achieve dichoptic presentation of the stimuli to the two eyes the liquid crystal shutter transmitted on alternate frames, light that is left or right circularly polarised, the changes in polarisation being synchronised to the picture presentation rate of 101 frames per second. Subjects wore glasses where the element covering each eye transmitted only one of the two polarisations of the light transmitted through the shutter. In this way each eye saw only one of the two interleaved video sequences, each eye receiving pictures at 50.5 frames per second. Subjects also wore normal corrective lenses as necessary. The total duration of the test sequences was seconds and up to 16 sequences were presented to each subject.

Subjects were asked to fixate a spot presented at the centre of the visual stimulus. Persons skilled in the art will recognise that other means of maintaining fixation, such as monitoring eye position could have been substituted without affecting the present demonstration. Evoked potentials were recorded with the samples being obtained synchronously with the rate of presentation of video stimuli. Faster sampling rates could have been used but for the present demonstration one sample per frame was used. Standard gold cup electrodes were placed on the scalp to record the evoked potentials. The dichoptic stimulus generation scheme and the VEP recording apparatus are illustrated in FIG. 2.

Figure 3:
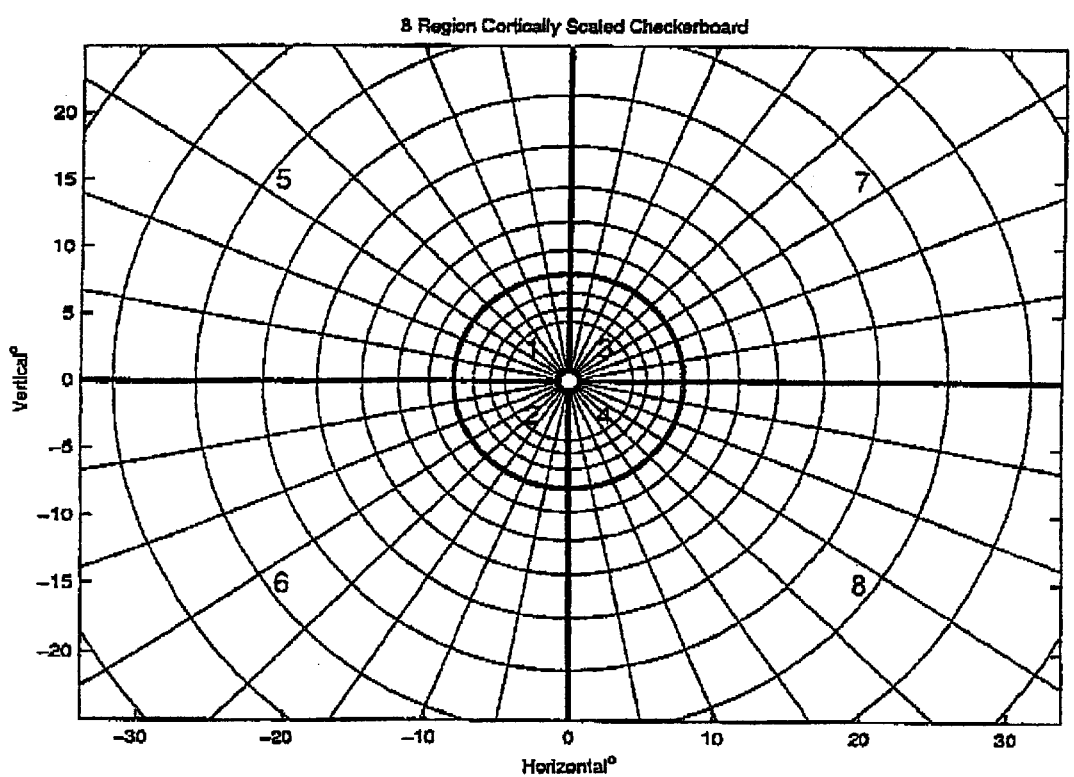
FIG. 3 shows a schematic representation of the visual stimulus used in the apparatus of this invention.

FIG. 3 shows a schematic representation of the visual stimulus used in the present demonstration, where checkerboard patterns with scales adjusted to match the magnification of the retinal projections onto the visual cortex are presented to eight different portions of the visual field, the separate regions being enumerated 1 to 8 respectively. The present diagram shows the boundaries of the individual checks. The boundaries of the eight regions are shown by the thicker black lines. In practice checkerboard patterns were formed by colouring every other check either black or white.

Figure 4:
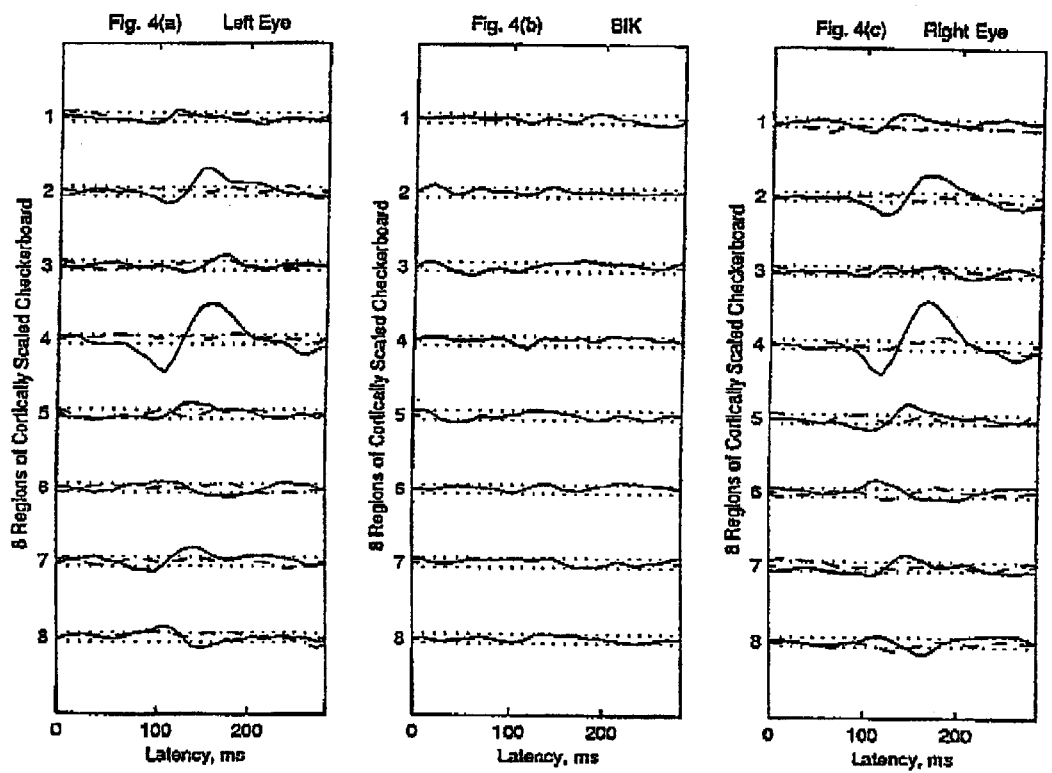
FIG. 4 shows the linear kernels (solid lines) and the first off-diagonal (dashed-lines), of the matrix of second order kernel coefficients estimated according to this invention for a normal subject, FIG. 4(a) corresponds to the left eye.

This scaling matches the well known magnification of the retinal neurons onto the visual cortex. Again, persons skilled in the art will recognise that other patterns, could have been substituted for the checks, and alternative scalings of the patterns could have been employed. In the present demonstration the contrast of the checks was reversed in time according to a pseudorandom sequence. In the present demonstration the pseudorandom sequence was either 1 or −1 at random with 50% probability of being in either state. In the one alternative demonstration the checks were coloured either black or white and the checks the temporal modulation sequence reversed their contrast. Contrast reversal of a given checkerboard indicates changing the black regions to white and the white regions to black. Mathematically we could represent the dark checks as having brightness −1 and bright checks as having brightness 1. On each frame of the stimulus sequence the pseudorandom sequence can adopt a value of −1 or 1, thus reversing the sign of the checkerboard contrast or leaving it unchanged. Kernels estimated with this contrast reversal stimulus are shown in FIG. 4. The visual stimuli employed in the eight regions of the stimulus reversed contrast in time according to a pseudorandom sequence. The plotted quantities in all cases are t-statistics with the same scaling applied to all the plotted waveforms. The pair of parallel dotted lines in each of FIGS. 4(a), 4(b) and 4(c) indicate the evoked potential amplitude beyond which the kernel coefficients are significant at the 95% level. The kernel waveforms shown are all the average of kernel estimates obtained over 4 repeats.

Figure 5:
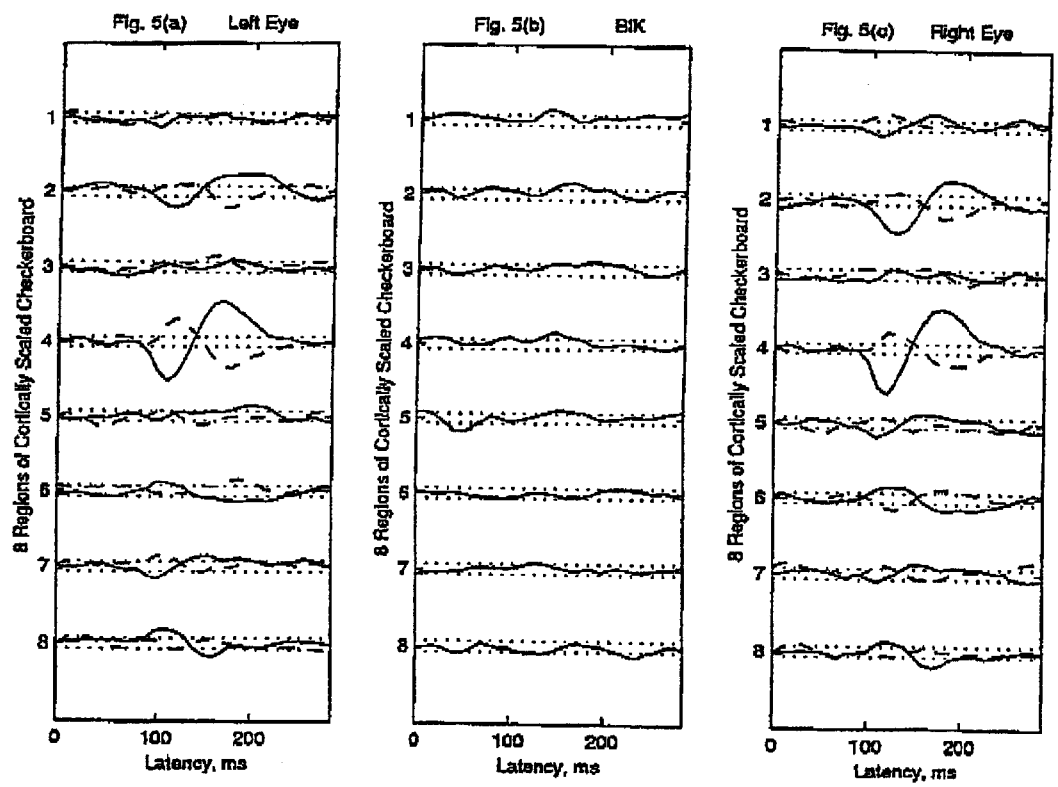
FIG. 5 shows similar results to FIG.4 using the same normal subject but different visual stimuli.

In a second alternative demonstration half the checks remained at the mean luminance of 50 nits while the alternate checks were modulated black or white. This alternative stimulus is referred to as a binary onset stimulus. Kernels estimated with this binary onset stimulus are shown in FIG. 5. The same normal subject was tested 4 times and the kernels averaged. The onset stimulus enhances the linear kernel amplitude compared to the contrast reversal case shown in FIG. 4 and also produces more reliable BIK waveforms.

Alternately, more than two brightness states can be used, for example a so-called ternary stimulus where checks can be one of black, white or grey presented with some set of probabilities can be used. Similarly, 4, 5 or some higher number of stimulus levels can be incorporated or the range contrasts employed could be lower than that spanned by the range black to white. Similarly some other image quality such as position, apparent depth or colour may be modulated. It is only important that the stimulus ensemble is sufficiently rich to permit estimation of the kernels by processes such as linear or logistic regression or related iterative methods: a stimulus will form an adequate basis in the mathematical sense when the model sub-space is spanned by the stimulus.

The video display was divided into 8 regions constituting 4 quadrants in both the central and peripheral visual field as illustrated in FIG. 3. The contrast of the checks within each of these 8 zones or regions changed coherently, that is all of the checks with a particular region reversed contrast together as determined by the pseudorandom temporal sequence applied to that region. Different temporal sequences where used to determine the sequence of contrast reversals in each of the 8 visual stimulus regions. Thus, on each frame of the stimulus sequence the checks within each of the 8 regions might reverse contrast or remain unchanged. Persons skilled in the art will recognise that partitionings of the visual field other than the 8 employed for the present demonstration could have been employed.

Coefficients for the linear, nonlinear and binocular interaction kernels (Equations 2 to 20 4) were then estimated by a least squares method permitting the calculation of error estimates and confidence limits on the coefficients. Kernel coefficients were estimated with a memory length, M in equations 1 to 4, of 300 ms, and coefficients for each of up to 16 repeats of the 30 second duration test sequences were estimated separately, kernel coefficients were then averaged across repeats. Other memory lengths could have been employed without diminishing the present demonstration. For the present demonstration the test signals were repeated, however, in a preferred design different sequences would be used on each repeat and the resulting kernels then averaged just as in the present demonstration.

Persons skilled in the art will appreciate that the quadratic nonlinear kernels (Equation 3) and the binocular interaction kernels (Equation 4) are 2 dimensional matrices of coefficients, the duration of response latency progressing along the diagonals of these 2 dimensional matrices. The different diagonals of these kernels represent interactions at different delays. For the present demonstration selected diagonals of these matrices of kernel coefficients were estimated by linear regression. These diagonal components are thus one dimensional waveforms like the linear kernels having dimensions on the abscissa of response latency in seconds, exactly as the linear kernels. Thus, we can present a set of one dimensional linear and nonlinear kernel waveforms which are sufficient for the present demonstration. Selecting a subset of the kernel coefficients also improves the error estimates for the coefficients in that the ratio of data points to the number of estimated coefficients is larger. In a preferred design all the coefficients of the entire quadratic and binocular interaction matrices would be estimated to obtain further information about the state of nerve conduction in a given subject.

FIG. 4 shows kernel waveforms for a normal subject where contrast reversing stimuli were employed. The latencies from the beginning of each waveform to the largest peaks in each kernel are indicative of the conduction latencies for each stimulus region and eye. Notice that different conduction latencies are obtained for different parts of the visual field implying different conduction latencies for each part of the visual field due to the rough retinotopicity maintained in the optic nerve. Compare for example the location of the peaks in the kernel waveforms for stimulus regions 2, 3, 4 and 6, 7, B. Obviously, if the stimulus regions were too small the relatively poor retinotopicity of the optic nerve would prevent independent latency data to be obtained for each stimulus. Some of the presently observed heterogeneity of the conduction latency in normal subjects will be due to different durations of nerve signal transmission within the eye. Nevertheless, the results are an obvious improvement over the case of recording a single gross evoked potential for the whole eye where the regional differences would be summed together into a single waveform. The results also show that results from the two eyes are similar as would be expected in a normal subject.

The kernel waveforms shown in FIG. 5 are from the same normal subject as for FIG. 4. In this case, however, binary onset stimuli were employed. This stimulus arrangement enhanced the linear kernel waveforms and also the BIK waveforms, thus providing more and better quality data.

Figure 6:
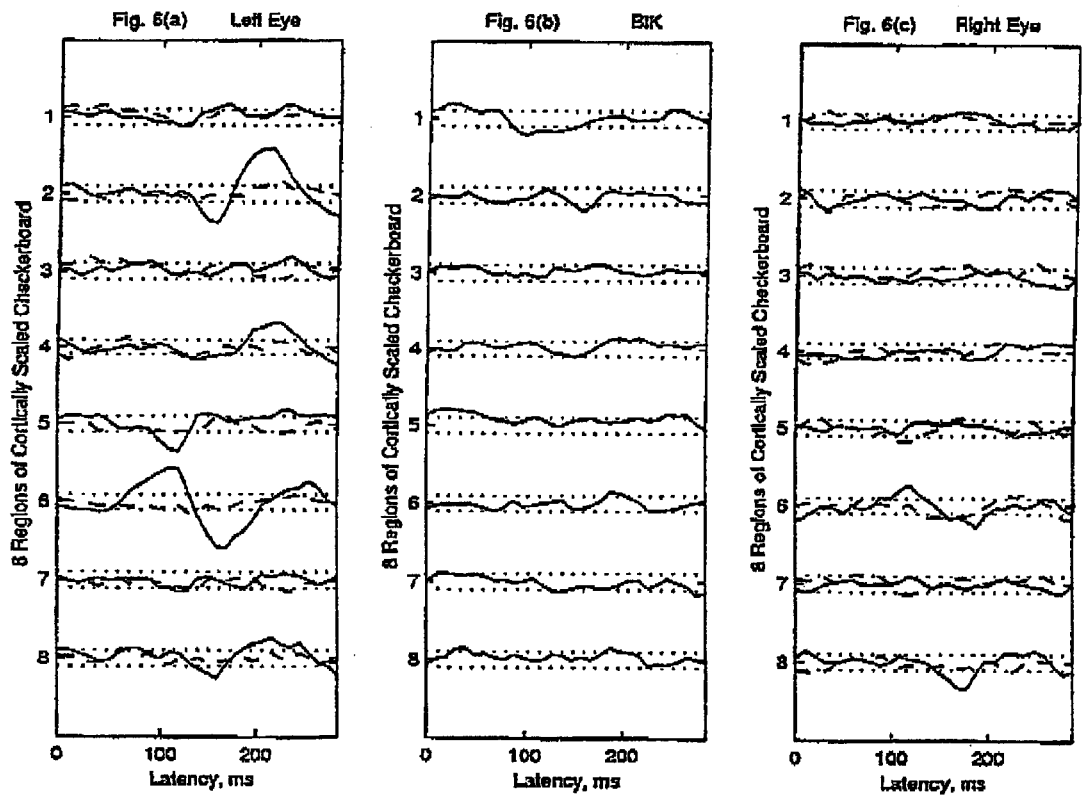
FIG. 6 shows results similar to FIGS. 4 and 5 for a person affected by multiple sclerosis.

The kernel waveforms presented in FIG. 6 were obtained from a subject with multiple sclerosis. The stimulus modality was contrast reversal as in the case of FIG. 4. Sixteen repeats were averaged for this subject. Some of the waveforms, such as those for the left eye for regions 2 and 4, show large increases in response latency compared to the data from normal subjects. The waveforms from the subject with multiple sclerosis also show decreased kernel amplitude and distortion of the kernels' shapes, particularly in the right eye kernels. This was consistent with the clinical presentation of the subject. The distortion may arise from a mixture of delayed and non-delayed nerve conduction within the component part of the optic nerve characterised by a particular kernel waveform. Kernels from the left and right eyes can either be substantially the same in terms of their latency, as in the kernel waveforms for region 8, or can be quite different as best shown by the left and right eye data for region 6. Of particular interest are the BIK waveforms for regions 4 and 6. While the delay for the BIK waveform of region 4 is much the same as for that for the optic nerve responses in FIGS. 6(a) and 6(b), the BIK waveform for region 6 is much more delayed at around 200 milliseconds, than either of the region 6 optic nerve waveforms in FIGS. 6(a) and 6(b). Thus, BIK waveforms can show increased response latency that can only be ascribed to conduction delays within a hemicortex. Since region 6 corresponds to the lower left half of the visual field the extra conduction delay is in the upper right hemicortex indicating disease in that brain area.

The kernel waveforms presented in FIGS. 4 to 6 demonstrate that it is possibie to simultaneously estimate binocular interaction kernels for the two visual cortices and kernels characterising conduction within both of the optic nerves, that supply separate information about the state of nerve conduction in each of these component parts of the visual nervous system. The present demonstration thus shows that the quite large stimulus regions employed permit even the relatively poor retinotopicity of the course of passage of individual nerve fibres within the optic nerves to be exploited to provide quite independent data on nerve conduction for each of the simultaneously presented visual stimuli employed. Even in normal subjects quite different conduction latencies for different component parts of their optic nerves can be observed, while subjects whose nerve conduction is affected by disease states can show both normal and abnormally long nerve conduction latencies in one optic nerve or hemicortex. Binocular interaction kernels can also show abnormality independent of latency changes observed in the optic nerve.

The foregoing describes only some embodiments of the invention and modifications can be made without departing from the spirit and scope of the invention.

What is claimed is:

1. A method of simultaneously assessing the function of component parts of the optic nerve, optic radiations and visual cortex, the method comprising the steps of:
   (a) dividing the visual field of view of each eye into a plurality of stimulus zones so as to roughly isolate confluent streams within the optic nerve, optic radiations and visual cortex due to their retinotopic arrangement;
   (b) presenting to the two eyes stimuli having different temporal modulation of the appearance of each of the zones of the visual field of each eye, the stimuli being different for each of the corresponding zones within the visual field of view of each eye;
   (c) making the temporal content of the variations of the appearance of the time varying stimuli sufficiently complex as to permit estimation of linear and nonlinear weighting functions characterising measured responses to each stimulus region and for each eye;
   (d) estimating some or all of the coefficients of the linear and nonlinear functions, for each stimulus zone, and binocular interaction, from the measured responses to said stimuli, to isolate separate contributions from component parts of the optic nerve, optic radiations and the left and right halves of the visual brain simultaneously.

2. A method as claimed in claim 1 wherein the linear and nonlinear weighting functions are Weiner or Volterra kernels.

3. A method as claimed in claim 2, wherein the visual field is divided into a zone centred on the central 6 to 12 degrees of the central visual field of view, and at least 4 surrounding zones.

4. A method as claimed in claim 3 wherein the surrounding zones split more peripheral visual field into quadrants defining the superior-nasal, superior-temporal, an inferior-temporary and an inferior nasal peripheral visual field.

5. A method as claimed in claim 2, wherein the latency to selected peaks within time course of the linear kernels is used as a measure of nerve conduction time with the component part of the optic nerve and optic radiations.

6. A method as claimed in claim 2, wherein the latency to some or all of the peaks along the diagonals of second order self quadratic kernels, and/or selected portions of higher order kernels are used to characterise different nonlinear responses.

7. A method as claimed in claim 6 wherein the different nonlinear responses are ON-OFF responses characteristic of sub-populations of neurones within the optic nerve.

8. A method as claimed in claim 2, wherein estimated binocular interaction kernels are compared with those obtained from known normal subjects to identify nerve conduction defects characteristic of damage within each hemicortex.

9. A method as in claim 8, wherein the nerve conduction defects are identified separately for selected stimulus zones.

10. A method as claimed in claim 9 wherein the selected stimulus zones are the inferior, superior, temporal and nasal zones of each half of the visual field.

11. A method as claimed in claim 2, wherein estimates of the kernel coefficients are obtained by means of logistic or linear regression and/or iterative methods.

12. A method as claimed in claim 11 wherein the coefficients are expressed as t-statistics.

13. A method as claimed in claim 1, wherein the stimulus includes modulation of the brightness of elements within each of the stimulus zones between two or three brightness levels and the function governing the alternation between the levels is approximately uniformly distributed noise.

14. A method as claimed in claim 13, wherein the stimulus includes modulation of an additional image parameter selected from the group or position, or apparent depth or colour of elements of the stimulus zones between two or three levels and the function governing the alternation between the levels is approximately uniformly distributed noise.

15. A method as claimed in claim 1, further including simultaneous stimulating one or more other sensory modalities where the temporal characteristics of these other stimuli are like those of each of the visual stimuli and interactions between each of the visual field zone stimuli and the other sensory modalities, and each of the other modalities, are determined to isolate brain responses from brain regions where those sensory modalities interact.

* * * * *